United States Patent [19]
Kelly

[11] Patent Number: 5,818,241
[45] Date of Patent: Oct. 6, 1998

[54] MOISTURE SENSOR USING HELICAL TRANSMISSION LINE

[76] Inventor: John M. Kelly, 9 Canon Ridge, Fairport, N.Y. 14450

[21] Appl. No.: 655,415

[22] Filed: May 30, 1996

[51] Int. Cl.$^6$ .................................................. G01N 27/12
[52] U.S. Cl. ........................... 324/640; 324/643; 324/694
[58] Field of Search .................................... 324/442, 445, 324/634, 637, 640, 642, 643, 694, 707

[56] References Cited

U.S. PATENT DOCUMENTS

| | | | |
|---|---|---|---|
| 2,752,586 | 6/1956 | Jordan | 324/694 X |
| 3,068,404 | 12/1962 | Moore et al. | 624/694 |
| 3,703,829 | 11/1972 | Dougherty | 73/290 R |
| 3,965,416 | 6/1976 | Friedman | 324/633 |
| 3,987,362 | 10/1976 | McCann et al. | 324/445 |
| 4,786,857 | 11/1988 | Mohr et al. | 324/643 |
| 4,949,076 | 8/1990 | Wann | 324/533 |
| 5,445,178 | 8/1995 | Fever | 137/1 |

OTHER PUBLICATIONS

"A New Instrument for the Measurement of Liquid Level" The Review of Scientific Instruments, vol. 41, pp. 1083–1087, Jul. 1970 (Lindstrom et al.).

"Electromagnetic Determination of Soil Water Content: Measurements in Coaxial Transmission Lines," Topp et al. pp. 574–582, Water Resources, vol. 16, Jun. 1980.

"A Method of Measuring Soil Moisture By Time–Domain Reflectometry," Lediev et al, Journal of Hydrology, pp. 319–328, 1986 (Month Unavaiable).

"Soil Moisture Measurement Using Portable Dielectric Probes and Time Domain Reflectometry," Brisco Et al. Water Resources Research, vol. 28, pp. 1339–1346, May 1992.

"Soil Moisture Sensors for Continuous Monitoring," Amer etal., Water Resources Bulletin, pp. 69–83, vol. 30, Feb. 1994.

"Calibrating Resistance—Type Soil Moisture Units in a High–Clay–Content Soil," Reynolds et al., Soil Science, vol. 144 pp. 237–241, Oct. 1987.

Sales Information Sheet for Water Content Reflectometer Model CS615–L, Campbell Scientific, Inc. Logan Utah, Dec. 1995.

*Primary Examiner*—Glenn W. Brown

[57] ABSTRACT

Moisture sensing apparatus that uses slow wave transmission lines. Such transmission lines include a helically wound inner core, a surrounding outer conductor, and a moisture bearing material between the inner core and the outer conductor. Preferably, the transmission line includes a moisture barrier that separates the transmission line into a sealed dry section and a wet section which is in moisture communication with its environment. The moisture sensing apparatus further includes a source of electrical signals on the transmission line, and a moisture sensing circuit, operatively connected to the slow wave transmission line, which senses the moisture content of the moisture bearing material from the velocity of the impressed electrical signals on the slow wave transmission line. Preferably, the velocity of the impressed electrical signals is obtained indirectly using a sing-around measurement technique.

19 Claims, 3 Drawing Sheets

MOISTURE SENSOR USING HELICAL TRANSMISSION LINE

FIELD OF THE INVENTION

This invention relates to moisture sensing instruments.

BACKGROUND OF THE INVENTION

Knowing the moisture content of materials is often very important. For example, soil moisture is fundamentally important to activities in agriculture, forestry, hydrology, and civil engineering. Knowing the moisture content of soil would enable farmers to tailor their activities to achieve crop yield optimization.

Because of the importance of knowing the moisture content of materials, various techniques have been developed to measure it. Three electronic techniques of measuring moisture are time domain reflectometry, capacitive sensing, and resistance sensing. Those techniques, which all depend upon the electrical properties of moisture, are suitable for continuous, relatively long term moisture sensing at a point location. Because the initial application of the present invention is soil moisture sensing, the following descriptions of those three techniques are directed to the particular application of soil moisture sensing. However, the principles of the present invention are not limited to soil moisture sensing.

In time domain reflectometry electromagnetic pulses are impressed upon a transmission line that includes a sensor probe portion. That probe portion is comprised of at least two conductors that are imbedded in the soil whose moisture is to be sensed such that the soil is between the two conductors. Disturbances in the transmission line cause reflections of the impressed pulses. By monitoring the reflections from the input end of the sensor probe (where an impedance mismatch between the sensor probe and a feed in transmission line causes a partial reflection) and the distal end of the sensor probe (which is usually either an open or a short, both of which create reflections), and by knowing the length of the sensor probe, the velocity of the pulse along the sensor probe can be determined. Since that velocity depends on the permittivity of the soil between the sensor probe conductors, which in turn depends upon the moisture content of the soil, the soil moisture can be found determined. More detailed information about prior art time domain reflectometry based soil moisture sensors can be found in Topp, "Electromagnetic Determination of Soil Water Content: measurement in Coaxial Transmission lines," *Water Resources Research,* vol. 16, pages 574–582, June, 1980; in Brisco et al., "Soil Moisture Measurement Using Portable Dielectric Probes and Time Domain Reflectometry," *Water Resources Research,* vol. 28, pages 1339–1346, May 1992, and in their citations.

Capacitive sensing has also been used with some success in determining soil moisture. For example, U.S. Pat. No. 5,445,178 entitled "Soil Moisture Sensor," issued to Feuer on 29 Aug. 1995 describes a capacitive sensor that is used as part of a frequency determining circuit of an inductor-capacitor oscillator. Interestingly, Feuer broadly claims inductor-capacitor oscillators used for sensing soil moisture, something that was previously described by D. Wobschall in "A Frequency Shift Dielectric Soil Moisture Sensor," *IEEE Transactions on Geoscience Electronics,* vol GE 16, pages 112–117 (Apr. 1978). In capacitive sensing capacitor plates are separated by the material whose moisture is being sensed, which is presumed to be soil. The capacitance of the capacitor then depends upon the permittivity of the soil, which in turn depends upon the soil's moisture content. As the permittivity of soil moisture is strongly frequency dependent, selection of the best operating frequency is important. Feuer suggests an operating frequency range of 10 KHz to 10 MHz, D. Wobschall suggests a measurement frequency range of about 10 MHz and 50 MHz, while Topp in the previously cited work indicates that the real part of the permittivity (dielectric constant) does not appear to be frequency dependent over the frequency range of 1 MHz to 1 GHz.

Resistance sensing is in some ways even simpler than time domain reflectometry and capacitive sensing. A resistance block is fabricated by placing a material that tends to maintain moisture equilibrium with its surroundings between two conductors. The resistance between the two conductors then depends upon the resistance of that material, which depends upon he moisture of that material, which in turn depends upon the moisture of its surroundings. Thus, after burial, the resistance of the block depends upon the soil's moisture. More detailed information about prior art resistance sensing can be found in Amer et al., "Soil Moisture sensors for Continuous Monitoring," *Water Resources Bulletin,* vol. 30, pages 69–83, and in he citations therein.

While time domain reflectometry, capacitive sensing, and resistance sensing can be used to determine the moisture content of soil and other materials, problems exist. Prior art time domain reflectometry systems have been too expensive for wide spread, continuous use particularly in remote locations. The cost of time domain reflectometry, at least to some extent, is a reflection (no pun intended) of the high speed equipment required to generate and sense short time duration pulses and to resolve the very short times between reflections. Capacitive sensing is strongly dependent upon the frequency of operation and of the soil type that is being measured. Furthermore, as capacitive sensing is dependent upon a stable oscillator, oscillator drift with time and temperature can be expected. While resistance sensing is less expensive then prior art time domain reflectometry systems, its accuracy, particularly in the long term, is not suitable for many applications. This is at least partially attributable to contaminates in the moisture that make the resistance of the material between the conductors depend upon things other than moisture.

The time domain reflectometry systems described above are closely related to those used in cable testing. Indeed, most prior art time domain reflectometry moisture sensing systems use cable testing time domain reflectometry units to generate the pulses and to sense the reflections. However, there exists an implementation of time domain reflectometry that does not require particularly fast electronics. That implementation incorporates a slow wave transmission line comprised of a helically wound inner conductor and a surrounding outer conductor. For example, K. Lindstrom, H. Kjellander, and C. Johnson in "A New Instrument for the Measurement of Liquid Level," *The Review of Scientific Instruments,* pages 1083–87, Volume 41, number 7, July 1970; describe a liquid level monitoring instrument in which electromagnetic pulses are impressed on a slow wave transmission line comprised of a helical wound inner conductor and a conductive outer shield which is spaced apart from the inner conductor such that a liquid can come between the inner conductor and the outer shield. Such slow wave transmission lines have a pulse velocity that is only a fraction of the velocity of an electromagnetic pulse in free space. Lindstrom et al's slow wave transmission line is inserted into a tank that holds a liquid whose level is being monitored. The time required for a pulse to be impressed on the transmission line, to travel down the transmission line, to reflect off of the interface between the liquid and a gas which fills the remainder of the wound transmission line, and to return to the point of impression is used to determine the position of the liquid-gas interface within the transmission line.

Slow wave transmission lines are advantageous because they change the problem of determining small time changes of a pulse traveling about 300,000,000 meters per second to the simpler problem of determining time changes of a pulse that travels much slower. For example, Lindstrom et al. reported a pulse speed of about 650,000 meters per second, while the inventor has built slow wave transmission lines with pulse speeds of less than 450,000 meters per second in air.

Not only does Lindstrom et al. disclose the use of slow wave transmission lines, they also disclose the use of sing-around to measure the distance to the liquid interface. Sing-around is advantageous since it provides a simple, reliable, relatively low cost method of converting pulse transient times into frequencies that are easily divided and measured. In Lindstrom et al.'s sing-around technique a pulse is impressed at the proximal end of their transmission line, that pulse travels along that transmission line until it is reflected by a material interface. After reflection the pulse travels back to the proximal end where it is processed to trigger another transmission line pulse. The process keeps repeating, producing a series of pulses at a frequency that depends upon the position of the material interface. The frequency of the series of pulses on the transmission line is referred to hereinafter as the transmission line oscillator frequency.

Lindstrom et al. note that their measurements are relatively inaccurate when the liquid-air interface is within either 15 centimeters of the top or 5 centimeters of the bottom of their transmission line. From this, and from experiments performed on similar transmission lines, I assume that the pulse speed on slow wave transmission lines is not uniform over the full length of the line. Furthermore, since the windings of slow wave transmission lines form inductors, and since the inductances of such inductors are known to be age and temperature sensitive, the pulse speed cannot safely be assumed constant with time and temperature. Subsequent experiments on slow wave transmission lines similar to those described in Lindstrom et al. indicate that the pulse speed of slow wave transmission lines is indeed neither uniform over the full length nor constant with time and temperature.

The sing-around transmission line oscillator frequency is obviously sensitive to changes in the time between reception of a reflection and the generation of the following pulse. Lindstrom et al.'s instrument addresses the problem by using high speed electronics to generate the following pulse during the reception of a reflection (the pulses overlap). This, as well as their use of a high speed comparator, reduces the sensitivity of their transmission line oscillator frequency to changes in time delays. While they describe the possible addition of a time delay, they do not discuss or address the sensitivity of the transmission line oscillator frequency to changes in the added time delay. However, Lindstrom et al. do note that changes in the liquid material cause changes in the transmission line oscillator frequency. This sensitivity can be considered a time delay in that the transmission line oscillator frequency changes represent changes in the time required for the reflection to achieve the comparator threshold (which in Lindstrom et al.'s instrument is fixed). Furthermore, it should be apparent that pulse attention over long slow wave transmission lines, particularly those with large winding diameters, can become relatively large. Such attenuation also causes a change in the transmission line oscillator frequency from that which it would be without pulse attenuation.

The sing-around transmission line oscillator frequency is also sensitive to changes in the characteristics of the materials that form the dielectric between the wound inner conductor and a conductive outer shield of the transmission line. Lindstrom et al. not only indicate that changes in the liquid material cause measurement changes (see the foregoing paragraph), but significantly to the principles of the present invention, they also indicate that their measurements are sensitive to changes in the gaseous material that fills part of their wound transmission line. Lindstrom et al. probably underestimate the material change-transmission line oscillator frequency change problem. For example, the permittivities of at least some liquids are temperature and frequency dependent.

Despite the above-mentioned problems, Lindstrom et al.'s instrument is impressive. They claim a reading accuracy of 0.02% of full scale and a small temperature dependency of 0.01% per degree Celsius. After testing devices similar to that described by Lindstrom et al. I believe that, at least in the short term, in a controlled environment, over a relatively small distance (about 1 meters), by carefully determining the system characteristics, and by avoiding liquid-air interfaces which occur near the ends of the wound transmission line such accuracy and temperature dependency is not unreasonable.

In view of the known sensitivity of the speed of electromagnetic signals on slow wave transmission lines to the permittivity of materials within the transmission line, in view of the relatively high permittivity of water as compared to most other materials, in view of the need for low cost moisture sensors, particularly soil moisture and water-in-oil sensors, in view of the limitations of prior art moisture sensors, in view of materials which tend to maintain moisture equilibrium with their surrounds, and in view of the performance of instruments as described in Lindstrom et al, a moisture sensor based on the sensitivity of the speed of electromagnetic signals to the moisture within a slow wave transmission line would be useful.

SUMMARY OF THE INVENTION

The principles of the present invention provide for a moisture sensing apparatus comprised of a slow wave transmission line, a source of electrical excitation which impresses electrical signals on that slow wave transmission line, a moisture bearing material within the transmission line, and a moisture sensing circuit, operatively connected to the slow wave transmission line, which senses the moisture content of the moisture bearing material. Beneficially, the moisture determining circuit uses the velocity of the impressed electrical signals on the slow wave transmission line. Preferably, the slow wave transmission line includes a dry section that does not contain moisture and a wet section that does include moisture. Then, the moisture in the wet section is beneficially obtained by comparing the velocity of the impressed electrical signals on the wet section to that of the dry section. Preferably, the velocity of the impressed electrical signals is obtained indirectly using a sing-around measurement technique.

Beneficially, the slow wave transmission line itself is comprised of a helically wound inner conductor and a surrounding outer conductor. Preferably, that slow wave transmission line includes a moisture barrier that separates the transmission line into a dry section and a wet section.

In one type of moisture sensing apparatus according to the principles of the present invention the moisture bearing material within the slow wave transmission line is a material that tends to assume the moisture of its surroundings. Beneficially, the slow wave device then includes numerous openings to assist moisture transfer from the surrounding environment into the material within the slow wave transmission line. If a moisture barrier is used, moisture is only allowed to enter the wet section of the transmission line.

In another type of moisture sensing apparatus according to the principles of the present invention the material inside the slow wave transmission line is taken from the surrounding environment. In such moisture sensing apparatus the surrounding outer conductor includes numerous openings to assist material transfer from the surrounding environment into the slow wave transmission line.

BRIEF DESCRIPTION OF THE DRAWINGS

Other aspects of the present invention will become apparent as the following description proceeds and upon reference to the drawings, in which.

Note that in the drawings, like numbers designate like elements. Additionally, the text includes directional signals that are taken relative to the drawings (such as right, left, top, and bottom). Those directional signals are meant to aid the understanding of the present invention, not to limit it.

DETAILED DESCRIPTION OF THE PREFERRED EMBODIMENT

Figure 1:
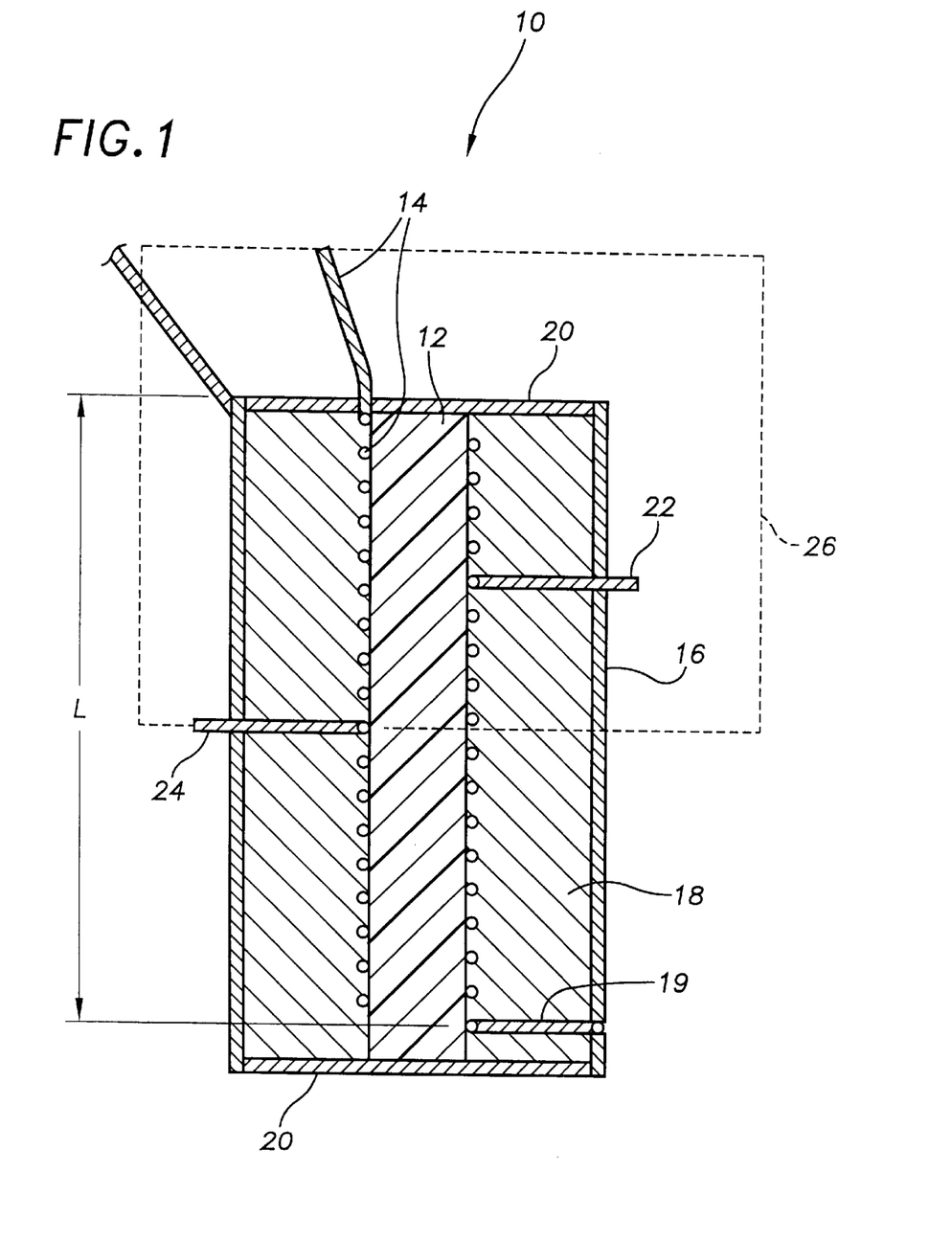
FIG. 1 is an unscaled, schematic, cut away view of a slow wave transmission line which is useful for practicing the present invention.

Reference is now made to FIG. 1, which shows a slow wave transmission line 10 that is useful for implementing moisture sensing according to the principles of the present invention. It is to be understood that, for purposes of explanation and clarity, the transmission line 10 is not drawn to scale. The transmission line 10 is somewhat similar to those described in Lindstrom et al. and in U.S. Pat. application Ser. No. 08/585,099, entitled "Time Domain Reflectometer Based Measurement System," that I filed on 16 Jan. 1996 and which is hereby incorporated by reference.

The transmission line 10 is comprised of a non-conductive inner core 12 that is wound by closely spaced windings of an insulated wire 14. While the radius of the core affects the speed of electromagnetic waves on the completed transmission line, the exact radius of the core is not critical. Lindstrom et al. taught an inner core having a radius of 40 mm and I think that is a good starting place. A larger core radius will result in a slower pulse velocity, but larger pulse attenuation. Furthermore, while the composition of the inner tube is not critical, it should not be conducting. Lindstrom et al. used a "perspex" tube and I've successfully used PVC pipe. For thermal stability and long term reliability I suggest that glass or phenolic tubing be used.

The radius and composition of the wire 14 that is wound around the inner core are also not critical. However, the smaller the wire radius the slower the speed of electromagnetic waves on the completed transmission line, but the greater the pulse attenuation. In view of the high ohmic resistance of very thin wire, and in view of the fact that winding the inner core with very thin wire is difficult to do, I suggest that one use a 32 gauge copper magnet wire. One might also want to experiment with physically stronger wire, such as steel.

While the radius and composition of the wire itself is not important, the insulation on the wire is. Single build magnet wires (magnet wire with a single coating of insulation) are subject to numerous pin holes in the insulation. As the underlying metal is exposed through those pin holes, and as corrosive environments can exist within the transmission line, wire protection is important for long term reliability. I suggest the use of multiple build wires (which have a thicker insulation), heat-shrink sleeving, or the application of a protective coating over the wrapped core.

Still referring to FIG. 1, the wound inner core is surrounded by a conductive outer shield 16. That outer shield is beneficially of a corrosion resistant material such as a stainless steel. For applications such as soil moisture sensing the outer shield should be perforated by many small openings to enable the surrounding soil to be in moisture communication with the interior of the transmission line 10. In such applications the outer shield beneficially takes the form of a cylindrical screen. In other moisture sensing applications, such as when determining the presence or amount of water-in-oil, the outer shield could, but need not, be solid, with the moisture bearing material entering into the transmission line from one end, possibly exiting from the other. It is therefore assumed that the outer shield 16 is a cylindrically shaped screen.

Still referring to FIG. 1, the bottom end of the wire 14 is beneficially shorted 19 to the outer shield 16. Alternatively, that end could be left open or, depending on the electronics used with the transmission line 10, it could be terminated in a resistance that is at or near the characteristic impedance of the transmission line. For example, if the transmission line is terminated in its characteristic impedance, a measurement technique based upon the phase shift of a harmonic wave could be used. However, the preferred embodiment of the present invention uses a sing-around measurement technique in which positive going pulses reflect off of the short 19 as negative going pulses that are used to trigger subsequent reflections. Thus, shorting the bottom end of the wire to the outer shield is beneficial.

In any event, disposed between the wound inner core and the outer shield is a moisture bearing material 18. That material can take two basic forms, it can be a sample of the material whose moisture is to be determined, or it can be a material that tends to moisture equilibrium with its surroundings. For example, if the transmission line 10 is to be used in an instrument that measures soil moisture, the material 18 could be soil. Alternatively, the material 18 could be comprised of a fiberglass, a plastic such as nylon, a composition such as gypsum, or of another material that tends to absorb or discharge moisture so as to obtain a moisture equilibrium with its surroundings and which has a permittivity significantly different than that of water. Relatively high resistance material is to be preferred, and metals are to be avoided.

The wound inner core is kept spaced apart from the outer shield by end spacers 20. If the outer shield is solid (no perforations) at least one of the end spacers should have one or more openings to enable moisture to contact the material 18.

Still referring to FIG. 1, the transmission line 10 includes a CAL tap 22 and a ZERO tap 24. Those taps are conductive leads connected to the winding and which provide for selective shorting of the transmission line 10 to the shield by the subsequently described external electronics. While the exact position of the CAL tap is not critical, as the purpose of the CAL tap is to provide a reference position which is below the section of the transmission line in which the pulse velocity is not uniform, the CAL tap should be placed where the pulse velocity is substantially uniform. For simplicity, I suggest that the CAL tap be placed about 25 cm from the top of the winding and the ZERO tap be placed half way between the CAL tap and the short 19.

The transmission line further includes a moisture barrier 26 that moisture isolates the section of the transmission line that is above the ZERO tap 24. That section is referred to hereinafter as the dry section, while the section of the transmission line below the ZERO tap is referred to hereinafter as the wet section. As moisture isolating the dry section can be rather difficult to do while keeping the material 18 constant throughout the transmission line, simply potting the dry section using a moisture stable material such as silicon RTV and forget keeping the material 18 constant throughout the transmission line is one approach. Alternatively, one could experiment with other ways of sealing the transmission line. Using a thin plastic ring-shaped insert that has a permittivity close to that of the material 18 and which snugly fits between the wound inner core and the outer shield is one idea. A thin bead of silicon adhesive applied to both radii of the insert then might be used to form a moisture proof bond and seal. In that case, the outer shield, if perforated, could be sealed simply by using a heat shrink plastic wrap and a small amount of sealant. In theory the alternative method is preferred and is therefore assumed in what follows. Maintaining the material 18 constant throughout the transmission line enables one to directly compare the subsequently described sing-around frequencies that result from having the CAL and ZERO taps selectively shorted. However, obtaining long-term, high quality moisture seals is difficult and one should expect to spend some time and effort to obtain them. While long-term, high quality seals are difficult, short term, lower quality seals are easy. Get a thin plastic ring and, using a liberal amount of RTV adhesive, glue it in place. Making the transmission line winding rather long reduces the impact of the resulting RTV globs and smears.

As previously mentioned, FIG. 1 is not to scale. To enable others, the following, together with the statements made above, provide a good starting point for implementing and experimenting with slow wave transmission lines: an inner core of a chemically and thermally stable, nonconductive material having a radius of around 40 mm, a winding of a 32 gauge magnet wire having a double or triple build (thicker insulation), an overall winding length of about 1 meter, an outer shield comprised of a stainless steel screen and having an inner radius of about 45 mm, a material 18 of fiberglass, CAL and ZERO taps of a 36 or 38 gauge magnet wire soldered to the 32 gauge magnet wire, the CAL tap at about 25 cm from the top of the winding, a ZERO tap halfway between the CAL tap and the short at the distal end of the transmission line, nylon end caps, a nylon ring which forms a moisture barrier, as much silicon RTV adhesive as required, and heat shrink tubing which fits over the dry section.

Figure 2:
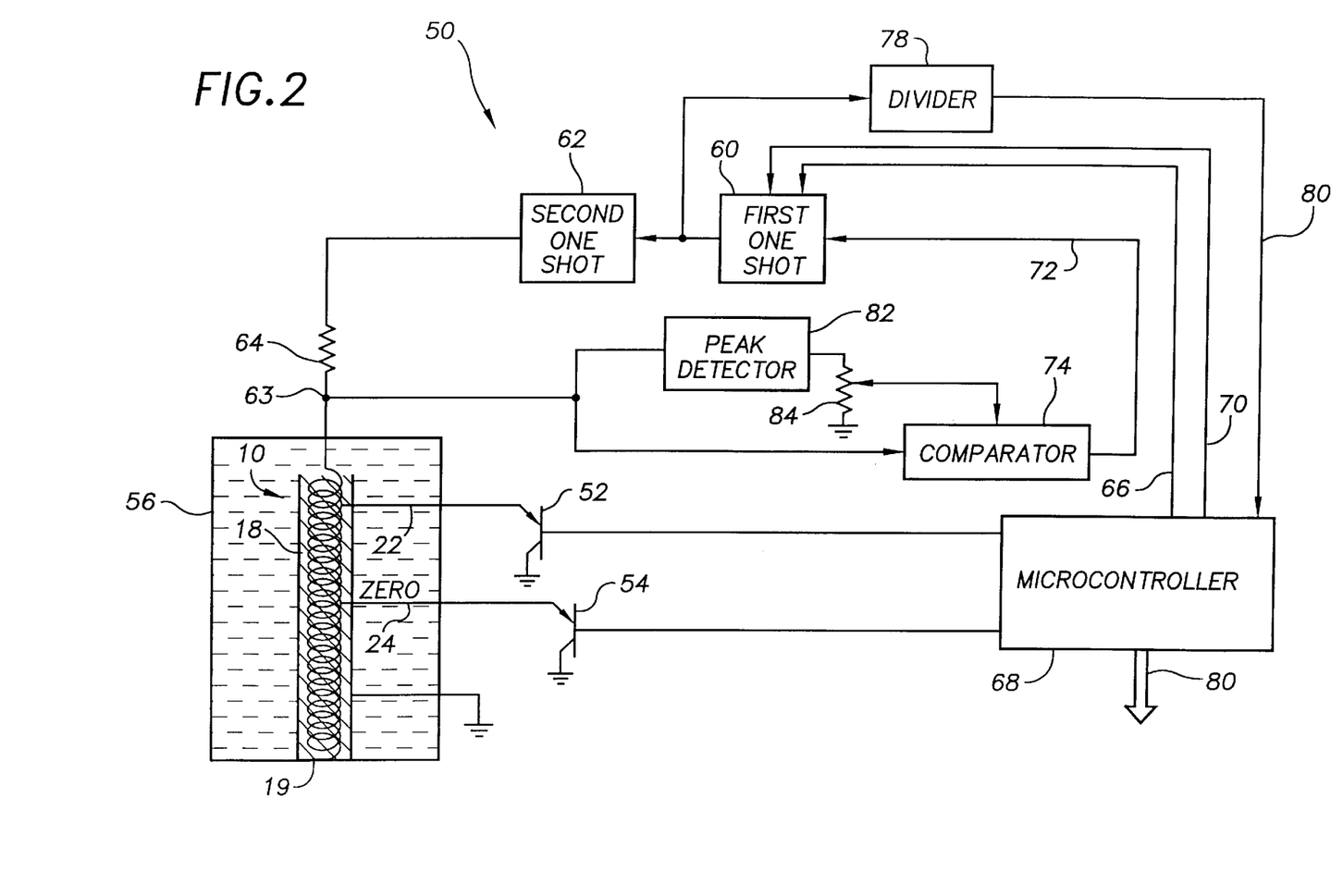
FIG. 2 illustrates, mostly in block diagram form, a preferred embodiment time-domain reflectometry based moisture sensing system that incorporates the slow wave transmission line shown in FIG. 1.

FIG. 2 shows a preferred embodiment time-domain reflectometry based moisture sensor 50 that incorporates the transmission line 10. As shown, the CAL tap 22 connects to a transistor 52 and the ZERO tap 24 connects to a transistor 54. Both of those transistors are configured to be selectively shorted to ground, that is, to the potential of the outer shield 16. While very low resistance shorts are not required, as should be clear after reading and reflecting on this document, a shorted tap should cause substantial reflections of pulses that are impressed on the transmission line.

As shown in FIG. 2, the transmission line 10 is inserted into an environment 56 whose moisture is to be measured. While the inventor has the particular environments of soil and oil in mind, the inventor is aware that the moisture content of other materials can be determined using the principles of the present invention. Therefore, the present invention is not to be limited by the particular environment 56.

Referring once again to FIG. 2, the moisture sensor 50 includes a first one shot 60 and a second one shot 62. When triggered by a pulse from the first one shot, the second one shot generates a fast rise time transmission line pulse that is applied to the an input node 63, and thus to the transmission line 10, via a resistor 64. The value of that resistor is beneficially selected such that reflections of transmission line pulses from the shorted distal end of the transmission line are strong over a full range of moistures and such that most or all of the reflections are absorbed by the resistor. While that best value for the resistor 64 depends on the construction of the transmission line and on the environment, and as some experimentation will be required, a value in the low kilohm range, at least for soil moisture sensors, can be anticipated. The value is perhaps best found using a high quality, non-inductive potentiometer in place of the resistor 64 and a pulse generator in place of the second one shot 62. As the potentiometer is varied the pulse reflection amplitude can be viewed on an oscilloscope. Simply maximize the pulse reflections and then determine the resistance value of the potentiometer.

The width of the transmission line pulse should be set such that it does not interfere with reflections from the CAL tap. That is, a transmitted pulse should return to zero at node 63 before the leading edge of a reflection from a shorted ZERO tap returns to the node 63. That is not much of a problem since the CAL tap can be kept well away from the top of the transmission line. More significantly, in some applications it may be beneficial to select a transmission line pulse width based upon the desired frequency of one or more Fourier components. As indicated above, D. Wobschall indicates that a good frequency selection for a soil moisture sensor is between about 10 MHz and 50 MHz, while Topp indicates that the permittivity of soil moisture does not appear to be frequency dependent over the frequency range of 1 MHz to 1 GHz, and Feuer suggest an oscillator frequency of between 10 KHz and 10 MHz. The inventor suggests that this is an area for further investigation.

One purpose of the first one shot 60 is to add a time delay between the triggering of the first one shot and the generation of the following transmission line pulse such that successive transmission line pulse do not interfere. The operation of the first one shot depends upon the state of a run signal on a run signal line 66 from a microcontroller 68; the occurrence of a start pulse on a start line 70, which is also from that microcontroller; and the occurrence of an oscillate pulse on an oscillate line 72 from a comparator 74. Beneficially the microcontroller 68 is a member of Philips' line of 87C750, 87C751, or 87C752 single chip microcontrollers.

Those microcontrollers are economical, provide sufficient memory to control the operation of the moisture sensor 50, have a good bit-control instruction set, and they have processing capabilities sufficient to perform various computations required to determine the moisture content from sing-around frequencies.

When the run signal is HIGH, an oscillate pulse induces a transmission line pulse by causing the first one shot to output a trigger pulse to the second one shot 62. The rising edge of the trigger pulse triggers the second one shot, causing it to generate a transmit pulse. When the run signal is LOW an oscillate pulses has no effect on the operation of the first one-shot. However, whether the run signal is HIGH or LOW, a start pulse causes the first one shot to generate a trigger pulse that triggers the second one shot. The trigger pulses to the second one shot are also input to a divider circuit 78 that divides the frequency of the trigger pulses (which is at the transmission line frequency when the transmission line is oscillating). The output of the divider circuit is applied to the internal timer of the microcontroller 68 via a line 80. Significantly, the state of the run signal enables or disables transmission line oscillations, while start pulses force transmission line pulses onto the transmission line 10.

Still referring to FIG. 2, the node 63 interconnects the proximal end of the transmission line 10, one end of the resistor 64, the input of a peak detector 82 and an input of the comparator 74. The peak detector 82 senses the negative peak of the pulse reflections and outputs a DC signal that is equal to the negative peak voltage to a potentiometer 84. The potentiometer divides that DC voltage by a given proportion (which is beneficially set during set up to about 85% of the peak) and applies the resulting proportional voltage, called hereinafter the trip-point voltage, to the other input, called hereinafter the trip-point input, of the comparator 74. The comparator then outputs an oscillate pulse to the first one shot 60 when the voltage on the node 63 goes below the trip point voltage. If the run signal is HIGH, an oscillate pulse induces a transmit pulse from the second one shot as explained above.

Setting the comparator trip point input at a voltage that is proportional to the negative peak of the reflection represents a significant improvement over the fixed comparator trip-point system disclosed in Lindstrom et al. In Lindstrom et al.'s instrument the frequency of the transmission line oscillations includes a variable component that relates to the time required for the reflections to reach the trip point. That is, if the reflection amplitude changed, so did the time required to reach the trip point. This trip-point sensitivity is a cause of the problem identified by Lindstrom et al. of a changing liquid in the tank causing variations in measurements. In contrast, by incorporating a comparator trip point that tracks the peak of the reflection the transmission line oscillator frequency becomes stabilized against changes in the amplitude of the reflections.

Peak detectors are well known and their designs are rather straightforward. Since reflections tend to be fast and since great precision is not required, the peak detector 82 uses a high-speed comparator. I have successfully used the design suggested in National Semiconductor's Linear Databook 1, 1988 Edition, on page 4–28, except that I use +5 and –5 volt supplies, an LM311 comparator, a .luF capacitor for C1, and a TLC271 op-amp for the op-amp buffer.

With the foregoing elements described I will now explain the operational sequence of the moisture sensor 50. First, the transistors 52 and 54 are forced off to cause the maximum pulse reflections to be from the distal end of the transmission line. It can be anticipated that those reflections will have peak magnitudes somewhat less than those which will result when one of the transistors is turned on. The microcontroller 68 then sets the run signal on run signal line 66 LOW to prevent transmission line oscillations. Then, 100 transmission line pulses are forced upon the transmission line by applying 100 start pulses on the start line 70. The 100 pulses are sufficient to enable the peak detector 82 and the potentiometer 84 to establish the proper trip point voltage for the comparator 74 at the given operating conditions. Each of the 100 transmission line pulses beneficially occurs such that only one transmission line pulse exists on the transmission line 10 at a time. This is achieved by delaying one transmission line pulse from the next by a period of time that is longer than the time required for a transmission line pulse to travel the full length of the transmission line and to return to node 63. The resistor 64, which is substantially matched to the impedance of the transmission line 10, absorbs the resulting reflections so as to significantly reduce or eliminate multiple reflections on the line. When the pulse reflections are more negative than the comparator trip point the comparator 74 sends oscillate pulses to the first one-shot. However, since the run signal is LOW, those oscillate pulses do not initiate additional transmission line pulses and transmission line oscillations do not occur.

After the 100 transmission line pulses have been forced on the transmission line, the microcontroller stops sending start pulses, but retains the run signal LOW. After a sufficient period of time all reflections on the transmission line have been absorbed by the resistor 64. Then, the run signal is taken HIGH to enable transmission line oscillations and one start pulse is applied to the first one shot to initiate transmission line oscillations. That pulse's reflection from the short 19 is detected by the comparator 74, which outputs an oscillate pulse to the first one-shot 60. Since the run signal is HIGH the one shot initiates another transmission line pulse and transmission line oscillations occur. The transmission line oscillator frequency (which is the same frequency as the trigger pulses) is divided by the divider circuit 78 and is applied to the microcontroller 68 as described above.

The microcontroller determines the number of internal clock timer periods, represented by the number $C_x$, which occur in one half of the period of the divided transmission line oscillator frequency when pulse reflections are from the short 19. The number $C_x$ is stored for later use. The one-half is because the internal clock timer is gated by the positive half of the divided transmission line oscillator frequency. In a very simple system the ZERO tap and the CAL tap might not be used at all. In that case, the value $C_x$ provides an indication of moisture. To determine moisture using just $C_x$, the value of $C_x$ that occurs when there is no moisture in the external environment must be known. Then, any deviation from that value is an indication of the moisture content of the system. Since one can expect a nonlinear relationship between the value of $C_x$ and moisture, the use of a look up table or a correction formula to equate $C_x$ to moisture will probably be required.

Figure 3:
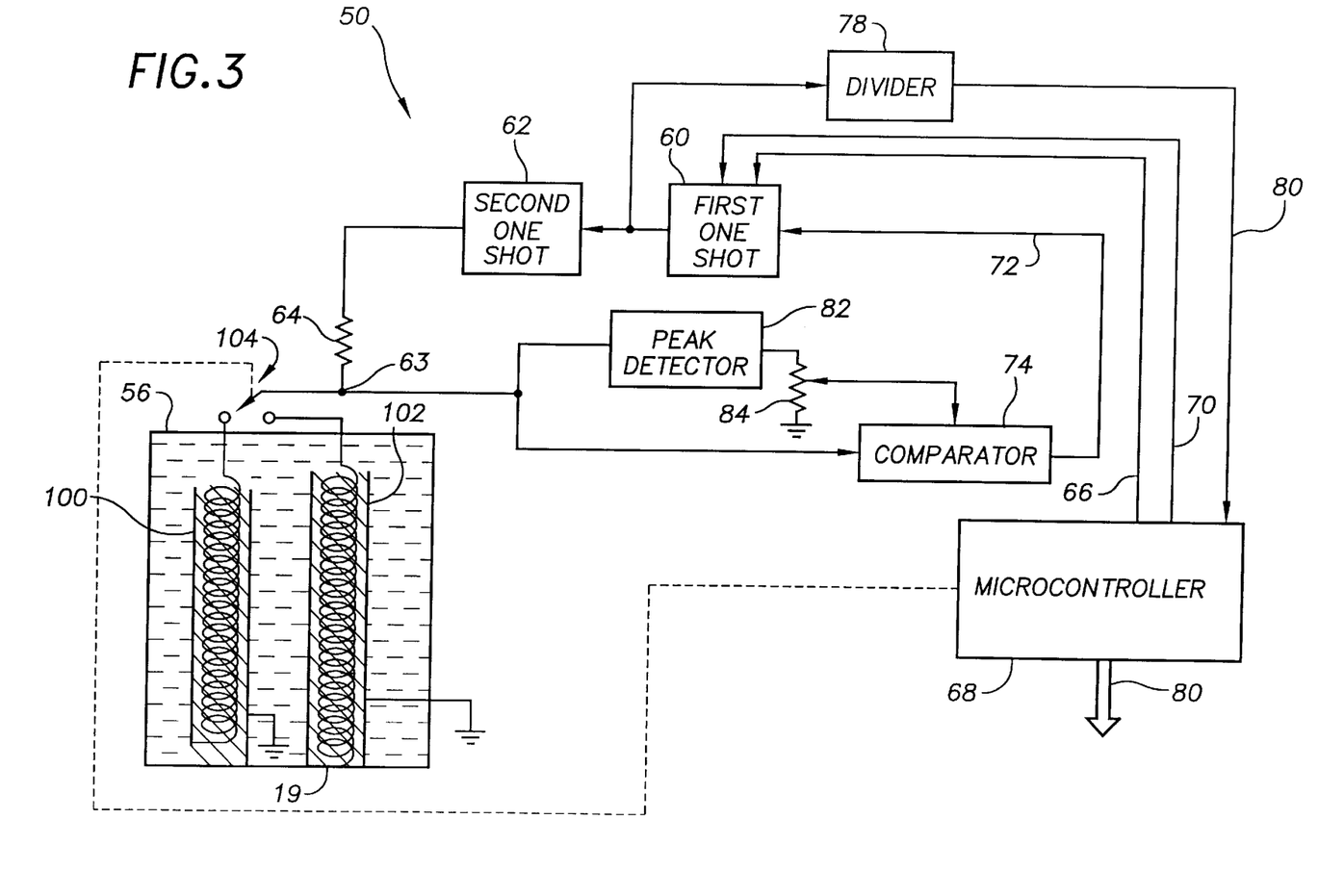
FIG. 3 illustrates, mostly in block diagram form, another embodiment time domain reflectometry based moisture sensing system that uses two slow wave transmission lines, one sealed from moisture, the other open to received moisture from the surrounding environment.

An alternative method of determining moisture without using CAL and ZERO taps is illustrated in FIG. 3. As shown, there are two transmission lines, transmission line 100 is open to moisture, while transmission line 102 is moisture sealed. Beneficially, except for transmission line 100 being open, the two transmission lines are substantially identical. For proper temperature compensation both transmission lines are beneficially located within the same environment 56. To determine moisture the value of $C_x$ for both transmission lines are determined by selectively connecting a switch 104 between node 63 and the inputs of transmission line 100 and transmission line 102. Beneficially, the position of switch 104 is controlled by the microcontroller 68. The difference between the two $C_x$ values is an indication of moisture. A digital value on bus 80 can then be used to control a look-up table or another device that signals the moisture content of the environment 56. While this method is accurate, it requires two transmission lines and a switch 104, and thus is not recommended.

Referring once again to FIG. 2, after the value of $C_x$ is determined, the microcontroller 68 shorts the transmission line at the ZERO tap position by turning on the transistor 54. The microcontroller 68 then sets the run signal on the run signal line LOW to prevent transmission line oscillations, and once again forces 100 transmission line pulses on the transmission line 10, again to enable the peak detector 82 to establish the proper trip point for the comparator 74, one that now relates to the shorted ZERO tap position. The microcontroller then stops sending pulses, but momentarily retains the run signal LOW. After all of the reflections on the transmission line have been absorbed by the resistor 64 the run signal is taken HIGH to enable transmission line oscillations and one start pulse is applied to the first one shot 60 to initiate transmission line oscillations. Then, the number of internal clock timer periods which occur during one half of the period of the divided transmission line oscillator frequency with the ZERO tap position shorted, represented by the number $C_{ZERO}$, is determined and stored for later use. Shorting the transmission line at the ZERO tap position represents a measurement within the moisture barrier 26. As the moisture barrier contains no moisture, the value Czero represents a reading of a shorted transmission line with zero moisture. It is of course possible to place a predetermined amount of moisture within the moisture barrier. That amount of moisture would then represent a reference amount of moisture. However, in the following it is assumed that there is no moisture within the moisture barrier.

The microcontroller then removes the short on the transmission line at the ZERO tap position by turning transistor 54 off, but shorts out the transmission line at the CAL tap position. Shorting the transmission line at the CAL tap position is useful for determining the time delay caused by the electronics and by the pulse transitions over the top part of the transmission line where the pulse velocity is not uniform. The microcontroller once again sets the run signal on the run signal line LOW to prevent transmission line oscillations and once again forces 100 transmission line pulses upon the transmission line so as to enable the peak detector 82 to establish the trip point (which now relates to the shorted CAL tap position) for the comparator 82 at the existing operating conditions. As before, the 100 transmission line pulses beneficially occur such that only one transmission line pulse exists on the transmission line at a time. After the 100 transmission line pulses have been forced onto the transmission line, the microcontroller stops sending start pulses, but momentarily retains the run signal LOW. After all reflections on the transmission line have been absorbed by the resistor 64, the run signal is taken HIGH to enable transmission line oscillations and one start pulse is applied to the first one shot 60 to initiate transmission line oscillations. Then, the number of internal clock oscillator timer periods that occur during one half of the period of the divided transmission line oscillator frequency with the CAL tap position shorted, represented by the number $C_{CAL}$, is determined. The number $C_{CAL}$ is stored for later use.

After the timer values $C_x$, $C_{ZERO}$, and $C_{CAL}$ are determined, the microcontroller 36 uses those values to determine a number which represents the moisture of the environment 56. That number is output on a bus 80 from which it can be used to signal moisture.

To determine the moisture, the value $C_{BASE}$ is determined by subtracting $C_{CAL}$ from $C_{ZERO}$. The value $C_{BASE}$ conceptually represents the time delay of pulses between the ZERO and CAL tap positions, which are within the dry section of the transmission line. As $C_{BASE}$ is within the environment 56, the reading of $C_{BASE}$ includes the effects of temperature on the transmission line oscillator frequency. Furthermore, the value $C_{BASE}$ will change because of the effects of aging. Then, to determine a value that corresponds to moisture in the environment, the value $C_{MOISTURE}$ is found from $C_{MOISTURE}=C_x-2(C_{BASE})$. The value of 2 comes about because it is assumed that the ZERO tap is midway between the CAL tap and the short 19. Of course scaling of the value of $C_{MOISTURE}$ is also possible.

The number $C_{MOISTURE}$ can be used in many ways. For example, one could simply use $C_{MOISTURE}$ directly as an indication of moisture, one could apply it to a lookup table that stores suitable conversions from possible values of $C_{MOISTURE}$ to moisture values in percent moisture by volume or by weight, or one could apply it to a formula to convert $C_{MOISTURE}$ to another quantity. Of course, using the value of $C_{MOISTURE}$ to control a 4–20 mA measurement circuits, or to control alarms or machinery is easily done.

It is to be understood that while the figures and the above description illustrate the present invention, they are exemplary only. Others who are skilled in the applicable arts will recognize numerous modifications and adaptations of the illustrated embodiments which will remain within the principles of the present invention. For example, while the foregoing has described the use of sing-around to determine quantities from which moisture can be derived, other methods can also be used. For example, one could use time of flight systems wherein pulses are generated on the transmission line and the time delay between transmission of a pulse and its reception at one or more of the CAL tap, the ZERO tap, or the short at the distal end of the transmission line, or reflections from those taps, are used to determine moisture. One could also use phase shift techniques to determine moisture. In such systems a known frequency could be generated at one end of the transmission line and the phase shift of that frequency along the line could be used to determine the moisture. Reference may be had to U.S. Pat. application Ser. No. 08/467,821, entitled, "Sensing and Measuring Properties Which Influence The Transit Time of a Wave," which I filed on 6 Jun. 1995, and which is hereby incorporated by reference, for phase shift techniques. Therefore, in view of the many alternatives to the embodiments described above, it is to be understood that the present invention is to be limited only by the appended claims.

What is claimed:

1. A moisture sensor assembly comprised of:
   a first transmission line having an inner core, a plurality of windings over said inner core, an outer conductor around said plurality of windings, and a moisture bearing material disposed between said inner core and said outer conductor;
   a source of electrical excitation for impressing electrical signals on said first transmission line; and
   an electrical network operatively connected to said first transmission line, said electrical network for sensing the moisture content of said moisture bearing material.

2. The moisture sensor assembly according to claim 1, where said moisture bearing material is comprised of fiberglass.

3. The moisture sensor assembly according to claim 1, where said moisture bearing material is comprised of plastic.

4. The moisture sensor assembly according to claim 3, where said moisture bearing material is comprised of nylon.

5. The moisture sensor assembly according to claim 1, where said moisture bearing material is comprised of soil.

6. The moisture sensor assembly according to claim 1, where said moisture bearing material is comprised of oil.

7. The moisture sensor assembly according to claim 1, where said moisture bearing material is comprised of gypsum.

8. The moisture sensor assembly according to claim 1, further comprising:
- a second transmission line having a second inner core, a second plurality of windings over said second inner core, a second outer conductor around said second plurality of windings, and a second moisture bearing material disposed between said second inner core and said second outer conductor;
- a switch for selectively connecting said source of electrical excitation to either said first transmission line or to said second transmission line such that electrical signals are selectively impressed on said first transmission line or on said second transmission line;
- wherein said electrical network is operatively connected to said second transmission line; and
- wherein said electrical network senses the moisture content of said moisture bearing material of said first transmission line by comparing the velocity of said impressed electrical signals on said first transmission line to the velocity of said impressed electrical signals on said second transmission line.

9. A moisture sensor assembly comprised of:
- a transmission line having an inner core, a plurality of windings over said inner core, an outer conductor around said plurality of windings, a CAL tap on said plurality of windings, and a ZERO tap on said plurality of windings;
- a source of electrical excitation for impressing electrical signals on said transmission line in response to trigger signals;
- a first switch for selectively shorting said CAL tap to said outer shield;
- a second switch for selectively shorting said ZERO tap to said outer shield;
- a receiver for receiving reflections of said electrical signals and for generating said trigger signals from said reflections;
- a controller for selectively switching said first switch and said second switch such that sing-around transmission line frequencies occur, said controller also for determining the moisture content of said moisture bearing material from said sing-around frequencies.

10. The moisture sensor assembly according to claim 9, further including a divider for dividing said sing-around frequencies and for applying the divided frequencies to said controller.

11. The moisture sensor assembly according to claim 10, where said moisture bearing material is comprised of fiberglass.

12. The moisture sensor assembly according to claim 10, where said moisture bearing material is comprised of plastic.

13. The moisture sensor assembly according to claim 12, where said moisture bearing material is comprised of nylon.

14. The moisture sensor assembly according to claim 10, where said moisture bearing material is comprised of soil.

15. The moisture sensor assembly according to claim 10, where said moisture bearing material is comprised of oil.

16. The moisture sensor assembly according to claim 10, where said moisture bearing material is comprised of gypsum.

17. The moisture sensor assembly according to claim 10, wherein said transmission line further includes a moisture barrier which divides said transmission line into a wet section for moisture communicating with its surrounds and a dry section which is moisture isolated from its surroundings.

18. The moisture sensor assembly according to claim 17, wherein said dry section includes the part of the transmission line between the CAL tap and the ZERO tap.

19. The moisture sensor assembly according to claim 10, wherein said winding of said transmission line is shorted at one end to said outer shield.

* * * * *